(12) United States Patent
Walzman (10) Patent No.: US 10,143,490 B2
(45) Date of Patent: Dec. 4, 2018

(54) DURAL KNIFE

(71) Applicant: Daniel Walzman, Bergenfield, NJ (US)

(72) Inventor: Daniel Walzman, Bergenfield, NJ (US)

( * ) Notice: Subject to any disclaimer, the term of this patent is extended or adjusted under 35 U.S.C. 154(b) by 0 days.

(21) Appl. No.: 15/040,601

(22) Filed: Feb. 10, 2016

(65) Prior Publication Data
US 2017/0224371 A1    Aug. 10, 2017

(51) Int. Cl.
*A61B 17/3211* (2006.01)
*A61B 90/30* (2016.01)
*A61B 90/00* (2016.01)

(52) U.S. Cl.
CPC .......... *A61B 17/3211* (2013.01); *A61B 90/03* (2016.02); *A61B 90/30* (2016.02); *A61B 2090/036* (2016.02); *A61B 2217/005* (2013.01)

(58) Field of Classification Search
CPC . A61B 17/42; A61B 17/4208; A61B 17/3209; A61B 17/32093; A61B 17/3211
See application file for complete search history.

(56) References Cited

U.S. PATENT DOCUMENTS

| | | | | | |
|---|---|---|---|---|---|
| 1,546,975 | A | * | 7/1925 | Feller | A22C 25/006 30/286 |
| 4,604,804 | A | * | 8/1986 | Sparks | A61F 15/02 30/162 |
| 5,341,822 | A | * | 8/1994 | Farr | B26B 5/00 128/898 |
| 5,423,842 | A | * | 6/1995 | Michelson | A61B 17/3213 30/294 |
| 5,896,667 | A | * | 4/1999 | Hawkins | B26B 1/00 30/2 |
| 6,471,577 | B1 | * | 10/2002 | Hendrickson | B26B 1/046 30/356 |
| 6,493,945 | B1 | * | 12/2002 | DeRosa | B26B 27/00 30/286 |
| 6,685,717 | B1 | * | 2/2004 | Ilic | A61B 17/320036 606/167 |
| 7,264,622 | B2 | * | 9/2007 | Michelson | A61B 17/025 606/80 |
| D553,466 | S | * | 10/2007 | Powers | D8/98 |
| 7,631,702 | B2 | | 12/2009 | Hansen | |
| 7,818,885 | B2 | | 10/2010 | Lafauci et al. | |
| D633,616 | S | | 3/2011 | Lafauci et al. | |
| 8,176,640 | B2 | * | 5/2012 | Gullicks | B26B 3/08 30/2 |
| 8,591,537 | B2 | | 11/2013 | Alleyne | |
| 9,107,695 | B2 | | 8/2015 | Horton et al. | |
| D788,303 | S | * | 5/2017 | Yurek | D24/147 |

(Continued)

OTHER PUBLICATIONS

DuraKnife, Dura Cutting Instrument Brochure and Surgical Guide, 2016, http://www.osteomed.com/Neuro/DuraKnife.aspx.

(Continued)

*Primary Examiner* — Julie A Szpira (57) ABSTRACT

A dural knife is provided with a handle, protector, and cutting element, wherein the protector is connected to one end of the handle and the cutting element connects to both the handle and the protector. More particularly, the dural knife has a protector shape and blade height that is adapted to safely raising the dura away from the cortex and making an incision in the dura while sliding the protector beneath the dura.

17 Claims, 4 Drawing Sheets

(56) References Cited

U.S. PATENT DOCUMENTS

| | | | | |
|---|---|---|---|---|
| 2002/0194734 A1* | 12/2002 | Huang | ................... | B26B 3/08 |
| | | | | 30/2 |
| 2006/0283609 A1 | 12/2006 | Hansen | | |
| 2007/0088374 A1* | 4/2007 | Masury | .............. | A61B 17/3211 |
| | | | | 606/167 |
| 2008/0243158 A1* | 10/2008 | Morgan | ............. | A61B 17/3213 |
| | | | | 606/167 |
| 2011/0087258 A1* | 4/2011 | Sluss | ............. | A61B 17/320016 |
| | | | | 606/170 |
| 2011/0106123 A1* | 5/2011 | Lafauci | .............. | A61B 17/3211 |
| | | | | 606/167 |
| 2014/0303609 A1* | 10/2014 | Marczyk | ............ | A61B 18/1482 |
| | | | | 606/29 |

OTHER PUBLICATIONS

CSAFE Device for C Sections Physicians Page, Aug. 2015, www.safe.US.

\* cited by examiner

FIG. 1 dura mater: and associated structures of the scalp, skull, and meninges (coronal view)

DURAL KNIFE

FIELD OF THE INVENTION

The described invention relates generally to cutting devices used during brain surgery.

BACKGROUND OF THE INVENTION

The described invention relates to dural cutting devices that may be operated manually, using a single hand.

Dura Mater

Figure 1:
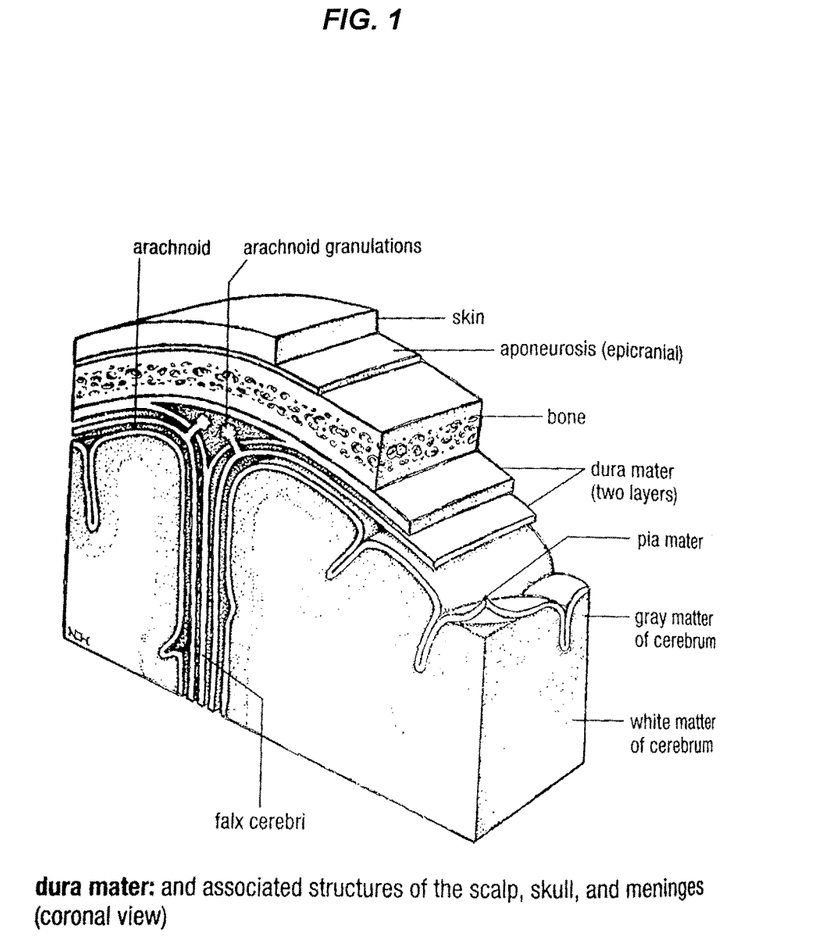
FIG. 1 shows the dura mater and associated structures. (Taken from Stedman's Medical Dictionary, 27th Edition, Lippincott Williams & Wilkins NewYork): 2000, page 548.

The dura mater is the dense fibrous layer of tissue that covers the brain and spinal cord of mammals. As shown in FIG. 1 (Stedman's p. 548), the dura is comprised of an inner meningeal layer and an outer periosteal or endosteal layer. The layers comprising the dura are fused together in most places, but separate where necessary to accommodate meningeal vessels and large venous (dural) sinuses, and where septa between brain regions are formed. The periosteal layer attaches directly to the inner surface of the skull and provides vascular and fibrous extensions into the skull bone. At the large opening in the base of the skull, which forms the passage from cranial to spinal cavity, the periosteal layer is closely adherent with bone, and is continuous with the dura matter of the spine.

The cellular and extracellular composition of the cranial dura mater includes fibroblasts, large amounts of extracellular collagen, and some elastic fibers arranged as flat layers. These structures are imperfectly separated by blood vessels and lacunar spaces to form the meningeal layer and the periosteal layer.

The outer, periosteal layer is rough and composed of fibers (i.e. is fibrillated) that adhere to the inner surface of skull bone. The adhesion to the inner skull is most pronounced opposite the immovable joints between skull bones (i.e. cranial sutures). The periosteal layer contains the blood vessels that supply blood to skull bone.

The meningeal layer has, on its inner surface, a layer of highly specialized elongated fibroblast cells named dural border cells. This layer does not contain any collagen and the cells lack cell junction connections. The cells of this layer are often separated by extracellular space that comprises amorphous non-filamentous material. The meningeal layer itself comprises two more layers: the compact lamella and the loose lamella. The compact lamella comprises tight fibrous tissue with few blood vessels, while the loose lamella does contain blood vessels.

The dura mater also is involved in the formation of the various dural folds or septa. The meningeal layer of cranial dura mater sends inward four septa (dural folds) that divide the cranial cavity into freely communicating spaces lodging the subdivisions of the brain. These folds are: (1) the falx cerebri, (2) the tentorium cerebelli, (3) the falx cerebelli, and (4) the diaphragma sellae.

The falx cerebri is a sickle shaped fold of dura mater that lays in the midline between the two cerebral hemispheres. It descends vertically from the longitudinal fissure between the hemispheres. The falx cerebri is narrow in the front of the skull near the root of the nose (i.e. where it is attached to the ethmoid bone at the crista galli) and is broader at the rear of the skull where it connects with the upper surface of the tentorium cerebelli. Its upper margin is convex and attached to the inner surface of the skull in the middle line. This attachment begins as far back as the internal occipital protuberance. The upper margin of the falx cerebri contains the superior sagittal sinus. Its lower margin is free and concave, and contains the inferior sagittal sinus.

The tentorium cerebelli is a cresent shaped fold of the dura mater that forms a roof over the posterior cranial fossa. It covers the upper surface of the cerebellum and supports the occipital lobes of the cerebral hemisphers. The tentorium cerebelli bounds a large oval opening in the anterior, which is used for transmission of the large bundle of corticofugal nerve fibers that pass longitudinally over the ventral surface of the midbrain on each side of the midline. This opening also allows transmission of sensory and autonomic fibers and other fiber tracts. The tentorium cerebelli is attached to the transverse ridges on the occipital bone. Three sinuses are related to the tentorium cerebelli: the straight sinus, which runs along the attachment of the tentorium to the falx cerebelli; the superior petrosal sinus, which runs along the attachment of the tentorium to the petrous bone; and the transferse sinus, which runs along the attachment of the tentorium to the occipital bone.

The falx cerebelli is a sickle shaped fold of dura that projects between the two hemispheres of cerebellum. It is attached anteriorly to the internal occipital crest, and its posterior free margin contains the occipital sinus. As it descends, the falx cerebelli sometimes divides into two smaller folds, which are lost on the sides of the foramen magnum.

The diaphragma sellae is a small circular horizontal fold, which covers a saddlelike prominence on the upper surface of the sphenoid skull bone located in the middle cranial fossa, dividing it in two halves. The diaphragma sellae also almost completely covers the pituitary gland. It contains a central opening that transmits the funnel-shaped extension of the hypothalamus connecting the pituitary gland to the base of the brain.

Blood Supply

The dura mater receives arterial supply from branches of numerous arteries. The several arteries that supply the dura of the anteria cranial fossa include the meningeal branches of the anterior and posterior ethmoidal arteries and of the internal carotid artery, and a branch from the middle meningeal artery. The middle meningeal artery is commonly damaged in head injuries. The several arteries that supply the middle cranial fossa include middle and accessory meningeal arteries of the internal maxillary artery, a branch from the ascending pharyngeal artery, which enters the skull through the foramen lacerum, and branches from the internal carotid artery, and a recurrent branch from the lacrimal artery. The posterior cranial fossa is supplied by meningeal branches from the occipital artery, one entering the skull through the jugular foramen, and another through the mastoid foramen; the posterior meningeal artery from the vertebral artery; occasional meningeal branches from the ascending pharyngeal artery, entering the skull through the jugular foramen and hypoglossal canal; and a branch from the middle meningeal artery.

The venous drainage of dura mater occurs by ways of meningeal veins that lie in the endosteal layer. The veins of the dura return blood via diploic veins or end in the various sinuses. Many meningeal veins open indirectly to the sinuses through a series of amplullae, called venous lacunae. These venous lacunae are located on either side of the superior sagittal sinus and are often invaginated with arachnoid granulations. The venous lacunae are also present near the transverse and straight sinuses. They connect with the underlying cerebral, diploic, and emissary veins.

Nerve Supply

The dura mater receives its nerve supply from branches of the trigeminal, glossopharyngeal, vagal, second and third spinal, sphenopalatine, optic nerve, and superior cervical ganglia. They supply both unmyelinated and myelinated sensory and autonomic fibers.

Brain Surgery

The dura creates an obstruction to reach the neural tissue of the brain and spinal cord, and therefore must be removed during many different types of brain surgery. The fibrous structure of the dura sometimes prevents visualization of the cortex after craniotomy is performed. Thus, during brain surgery, an opening in the dura must be made, requiring cutting. Cutting of the dura must be made with great care because, as described above may blood vessels and nerves innervate the various dural processes.

First, removal of the bone flap during craniotomy must be performed gently because, in certain areas, the inner skull may be adhered to the outer dura, possibly resulting in tearing of dura which can cause extensive bleeding and damage the underlying cortex.

After careful removal of the bone flap, the surgeon must create a surgical flap in the dura to gain access to underlying cortical structures. This procedure is critical, and an unsteady hand or improper tool can result in damage to the underlying brain structures or blood vessels within the dura, e.g., the arteries which supply the dura with oxygen and nutrients, flow between the inner surface of the skull and the dura, and injury to the arteries in the dura can have serious consequences. The middle meningeal artery, which flows underneath the temporal-parietal skull region, for example, is commonly damaged during dural incision. Such damage can result in an epidural hematoma, and, if not controlled, can lead to increased intra-cranial pressure, cortical damage, and ultimately death of the patient. Moreover, the septal folds define the dural sinuses, and venous drainage is funneled through the invaginations into the jugular venous system. The dura sinuses roughly follow the suture lines of the cranium, and performing operations close to the suture lines may cause damage to the sinuses, causing serious bleeding that is difficult to control.

During incision and retraction of the dura matter, major dural blood vessels and any communicating vessels should be avoided if possible, or cauterized with bipolar cautery if necessary.

Although incision of the dura can be performed in a number of ways, great care is required to avoid damage to the underlying cortex. Generally, the dura is first lifted slightly off the cortex using a dura hook (tissue pick), or alternatively by pushing a threaded needle through the outer dura layer and pulling up. Next, an incision is made by nicking the dura using a scalpel blade, with the cutting edge of the blade held upward.

Alternative methods for cutting the dura exist. For example, in one method, microdissection scissors may be inserted into the nick and used to finish the incision via successive cuts. Alternatively, the dural incision can be completed by lifting the adjacent dura and sliding the flat end of a Woodson neurosurgical elevator (a neurosurgical instrument having at least one flat blade with smooth edges approximately 13 mm long and 3 mm wide) under the dura, using it to gently lift the dura away from the brain while cutting directly on the flat surface of the Woodson with a scalpel knife. In some versions the blade of the instrument has a groove along its length. The scalpel knife is placed on the blade, and the Woodson and knife can be advanced together, with the knife cutting the dura sliding on top of the Woodson and the brain remaining protected.

The microdissection scissors are not ideal because they are not able to make a continuous incision. The Woodson technique for incising the dura is not ideal because it requires using two hands in a sometimes awkward position, or requires an assistant to hold one of the two instruments and coordinate the effort.

There exists a need for improved dural cutting devices that make cutting the dura in brain surgery easier and safer by minimizing the risk of inadvertent injury to an underlying blood vessel of the brain tissue that can be operated efficiently by a surgeon.

BRIEF SUMMARY OF THE INVENTION

According to some embodiments, the dural knife comprises a handle having a front, a back, a first end, and a second end; a protector having a top, a bottom, a rounded tip, and a heel, the second end of the handle connected to the top of the protector at the heel end. According to some embodiments a horizontal distance between the rounded tip and the heel defines a total length of the protector, and wherein the vertical distance between a most distal part of the top and a most distal part of the bottom defines the height of the protector. According to some embodiments, the dural knife comprises a cutting element connected to the handle and the protector, the cutting element having a cutting edge that merges with the front of the handle and with the top of the protector. According to some embodiments, a vertical distance between a point where the cutting edge merges with the front of the handle and the most distal part of the bottom of the protector defines the combined height of the cutting element and protector. According to some embodiments, the dural knife comprises a region on the top of the protector between the rounded tip and the point where the cutting edge merges with the top of the protector defines a fore top, and a horizontal distance between the point where the cutting edge merges with the top of the protector and the rounded tip defines the length of the fore top. According to some embodiments, a vertical distance between the point at which the cutting edge merges with the front of the handle and the point at which the cutting edge merges with the protector defines the height of the cutting element. According to some embodiments, the height of the cutting element is at most 85% of the combined height of the cutting element and protector. According to some embodiments, the height of the protector increases continuously from the rounded tip for over 10% to 90% of the total length of the protector, then decreases or remains constant for a remaining distance of the total length, wherein the protector bottom remains flat over 90% or more of the total length of the protector. According to some embodiments, the fore top of the protector has a length of at least 25% of the total length of the protector. According to some embodiments, the dural knife is adapted to safely raise the dura away from nervous tissue of the brain or spinal cord during continuous incision of the dura.

According to some embodiments, the cutting element of the dural knife is a blade. According to some embodiments, the cutting element height is approximately 50% of the combined height of the cutting element and protector. According to some embodiments, the height of the protector increases continuously from the rounded tip over approximately 50% of the total length of the protector, then decreases or remains constant for the remaining distance of the total length, wherein the protector bottom remains flat over 90% or more of the total length of the protector.

According to some embodiments, the length of the fore top is at least 30% of the total length of the protector. According to some embodiments, the protector further comprises a light source. According to some embodiments, the protector further comprises a light source in the rounded tip. According to some embodiments, the protector further comprises a light source in the top of the protector. According to some embodiments, the handle further comprises a mechanism that controls the light source.

According to some embodiments, the protector further comprises a suction opening and channel, through which fluids can be drawn away from the protector. According to some embodiments, the handle further comprises a mechanism that controls a force of suction drawing fluids away from the protector.

According to some embodiments, the cutting edge of the dural knife is straight and is positioned at an angle of 120 degrees or more relative to the top of the protector. According to some embodiments, the cutting element of the dural knife is a cauterizer.

These and other advantages of the invention will be apparent to those of ordinary skill in the art by reference to the following detailed description and the accompanying drawings.

DETAILED DESCRIPTION

In the various views of the drawings, like reference characters designate like or similar parts.

Figure 2:
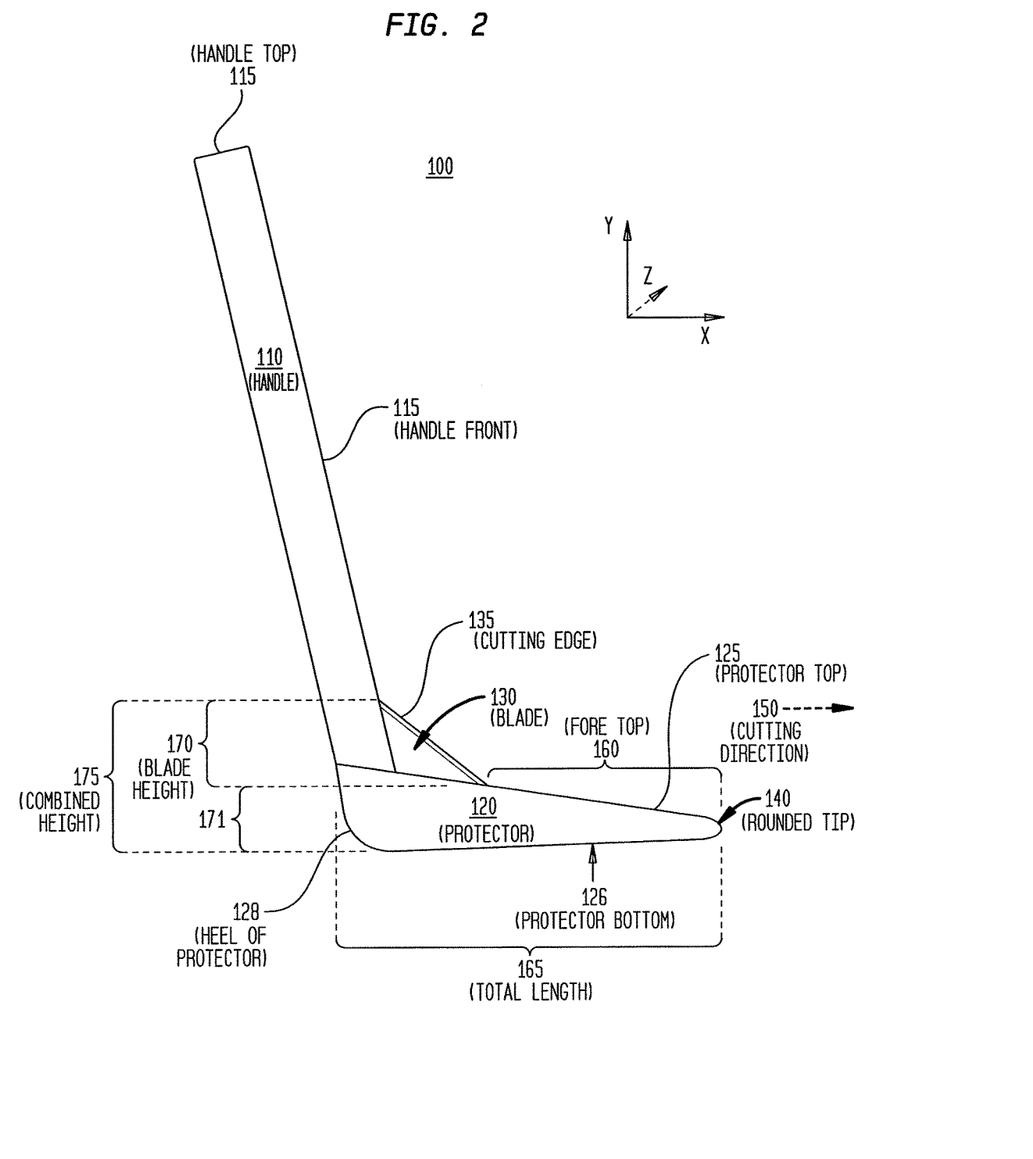
FIG. 2 illustrates a side view of one embodiment of the described invention.
Figure 3:
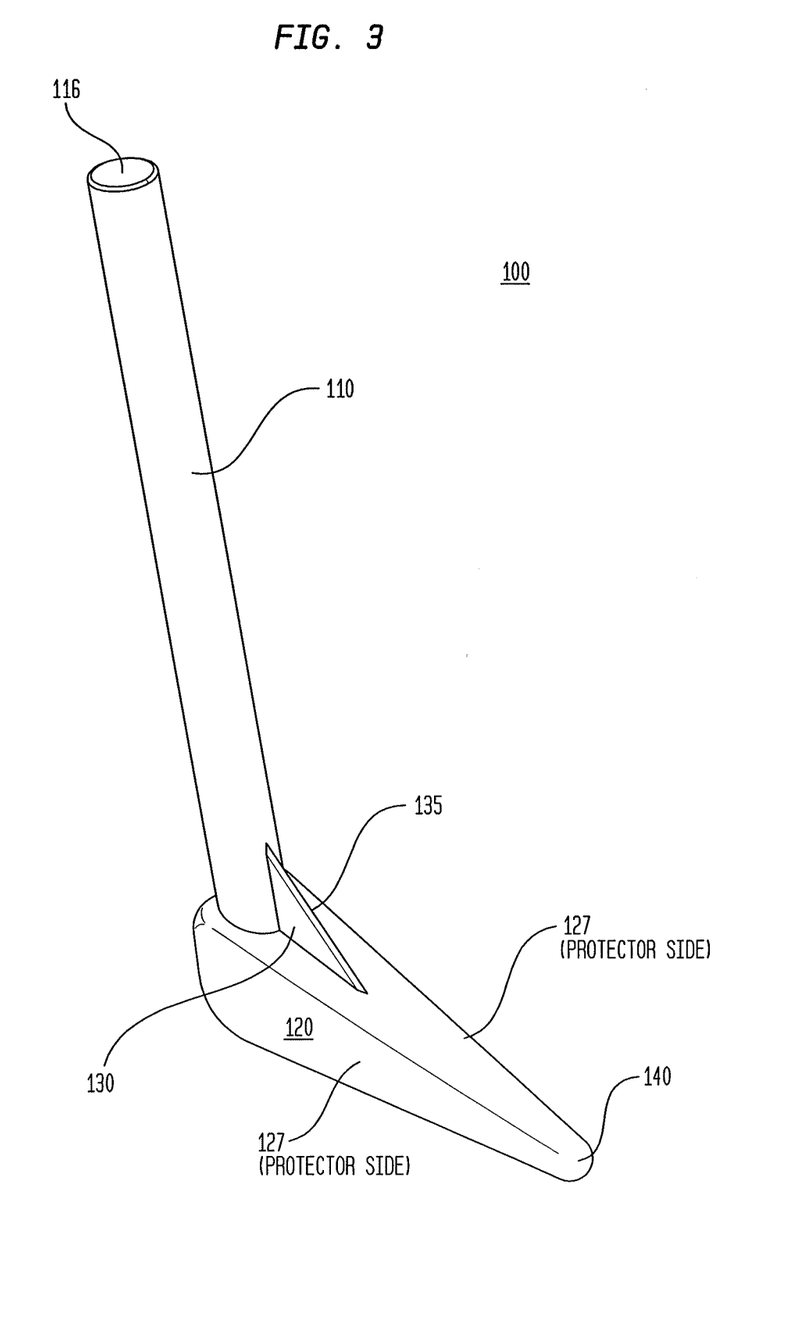
FIG. 3 illustrates a perspective view of one embodiment of the described invention.

FIGS. 2 and 3 shows an exemplary and non-limiting example of one embodiment of the dural knife 100 of the described invention. FIG. 1 illustrates a side view of the dural knife 100 comprising a handle 110, protector 120, and blade 130 assembled in one possible configuration.

According to some embodiments, the handle 110 is elongated and shaped to be gripped by a human hand and is connected on one end to protector 120. According to some embodiments, the handle 110 and the protector 120 are attached to one another at an approximately 120 degree angle. According to some embodiments, the handle 110 may be attached to the protector 120 at angles in the range of 20 degrees to 170 degrees, in the range of 40 degrees to 120 degrees, in the range of 60 degrees to 100 degrees, or at approximately 90 degrees. According to some embodiments, the handle has the approximate dimensions of the handle on the Woodson neurosurgical elevator.

According to some embodiments of the described invention, the angle at which the handle 110 is connected to the protector 120 is fixed. According to some embodiments, the invention comprises a movable joint that allows the angle of the handle 110 to the protector 120 to be modified according to user preference. For example, some embodiments of the invention employ a rotational joint, such as a knuckle joint, as the interface of the handle 110 to the protector 120. Such a knuckle joint interface may comprise a single eye component, a double eye component, and a knuckle pin. According to some embodiments, the handle comprises the double eye component, while the protector comprises the single eye component. According to some embodiments, the handle comprises the single eye component, while the protector comprises the double eye component. According to of the aforedescribed embodiments, the eyes would be aligned and a knuckle pin would be inserted to create the joint. According to yet other embodiment, each of the handle and protector may comprise multiple eyed components, which are held together by a pin. According to embodiments wherein the angle of attachment of the handle 110 with the protector 120 is variable, an appropriate locking mechanism can be employed to fix the angle at the user's desired setting.

According to some embodiments of the described invention as depicted in FIGS. 2 and 3 the blade 130 is located near the intersection of the handle 110 and the protector 120. According to some such embodiments, the blade has a flat cutting edge 135 facing outward away from the handle 110 and the protector 120. According to some such embodiments, the blade is attached to the handle front 115 and the protector top 125, and a closed tracing of the cutting edge 135 handle front 115 and protector top 125 forms an obtuse triangle.

According to some embodiments, the blade 130 is connected to the top of the protector at an obtuse angle. According to some embodiments, the blade 130 is connected to the top of the protector at an angle of 90 degrees or more. According to some embodiments, the blade 130 is connected to the top of the protector at an angle of 100 degrees or more. According to some embodiments, the blade 130 is connected to the top of the protector at an angle of 110 degrees or more. According to some embodiments, the blade 130 is connected to the top of the protector at an angle of 120 degrees or more. According to some embodiments, the blade 130 is connected to the top of the protector at an angle of 130 degrees or more. According to some embodiments, the blade 130 is connected to the top of the protector at an angle of 140 degrees or more. According to some embodiments, the blade 130 is connected to the top of the protector at an angle of 150 degrees or more. According to some embodiments, the blade 130 is connected to the top of the protector at an angle of 160 degrees or more. According to some embodiments, the blade 130 is connected to the top of the protector at an angle of 170 degrees or more.

According to some embodiments, the protector top 125 has a substantial length preceding the cutting edge 135 of the blade. This region is labeled "fore top" 160 in FIG. 2. For example, according to some embodiments, the length of the fore top 160 is approximately ½ the total length 165 of the protector. According to some embodiments, the length of the fore top 160 is a fraction of the total length 165 of the protector, e.g, at least 20%, 25%, 30%, 35%, 40%, 45%, 50%, 55%, 60%, 65%, 70%, 75%, or 80%. Although the area of the fore top 160 is depicted with a straight cutting edge 135, the fore top is not limited to this embodiment. For example, the fore top 160 may be present with a convex or concave cutting edge that begins at the point where the cutting edge merges with the protector top 125. Similarly, the total length 165, which may be measured regardless of the protector shape, can begin at the heel 128 of the protector and end at the most distal point on the rounded tip 140.

The combined height 175 of the blade and protector is the vertical distance between the point where the cutting edge merges with or intersects the front of the handle and the lowest point on the bottom of the protector. The blade height 170 is the vertical distance between the point at which the cutting edge merges with the handle front and the point at which the cutting edge merges with the protector. According to some embodiments, the blade height 170 is in the range of 20% to 80% of the combined height 175 of the blade and protector (i.e., at least 20%, at least 25%, at least 30%, at least 35%, at least 40%, at least 45%, at least 50%, at least 55%, at least 60%, at least 65%, at least 70%, at least 70%, at least 80%, or no more than 80%, no more than 75%, no more than 70%, no more than 65%, no more than 60%, no more than 55%, no more than 50%, no more than 45%, no more than 40%, no more than 35%, no more than 30%). According to some embodiments, the blade height 170 is in the range of 40% to 70% (i.e., at least 40%, at least 45%, at least 50%, at least 55%, at least 60%, at least 65%, at least 70%, or no more than 70%, no more than 65%, no more than 60%, no more than 55%, no more than 50%, no more than 45%, no more than 40%), of the combined height 175 of the blade and protector. Although the blade height 170 is depicted in FIG. 1 with a straight cutting edge 135, the blade height is presented with other embodiments of the blade. For example, the blade height 170 measurable with a convex or concave cutting edge begins at the point where the cutting edge 135 merges with the handle front 115. Similarly, the combined height 175 may be measured regardless of protector shape and begins at the point at which the cutting edge 135 merges with the handle front 115 and ends at the most distal point on the protector bottom 126.

According to some embodiments, the blade 130 may have a flat cutting edge 135 that is at an angle greater than or less than 90 degrees relative to the direction in which the dural knife is intended to be moved along the dura. That direction is the cutting direction depicted by arrow 150 in FIG. 1. For example, in the embodiment depicted in FIGS. 1 and 2, the cutting edge 135 of the blade is at an approximately 120 degree angle relative to the cutting direction. Thus, in that embodiment, the cutting edge 135 contacts the dura sliding over the protector at approximately 120 degrees. According to some embodiments, the angle of the cutting edge 135 may be greater than or less than 120 degrees relative to the cutting direction. According to some embodiments, the blade 130 may be affixed to the handle 110 or protector 120 in a manner that allows for altering the cutting edge angle according to user preference. According to some embodiments, the cutting edge angle may be dictated by the changeable angle of the handle relative to the protector. For example, according to some embodiments the blade 130 may comprise a rotatable joint that is affixed to the protector, which provides a fixed pivot point, combined with a locking mechanism on the handle that allows for variable placement of blade attachment along the length of the handle. According to some embodiments, the blade 130 may comprise a rotatable joint that is affixed to the handle, which provides a fixed pivot point, combined with a locking mechanism on the protector that allows for variable placement of the blade attachment along the length of the protector. According to either embodiment, changes in the angle of attachment between the handle and the protector may be accompanied by changes in the angle of the cutting edge relative to the direction of cutting.

According to yet other embodiments, changes to the cutting edge angle may be made independently of the angle of the handle 110 relative to the protector 120. For example, according to some embodiments, the handle and the protector each comprise a locking mechanism that allows for variable placement of the blade attachment position along the length of either the handle or protector. Thus, the angle of the cutting edge of the blade may be altered regardless of whether the angle of the handle relative to the protector is changed.

According to some embodiments, the blade 130 is permanently affixed to one or more of the handle 110 or the protector 120. According to some embodiments, the blade 130 is removably attached to the handle 110 or the protector 120, and may be replaced with other blades when necessary.

According to one aspect of the described invention, the dural knife is used by inserting rounded tip 140 into a small pre-made incision in the dura, thus resting the dura on protector top 125. A small region of the dura may then be raised from the brain by raising the protector, and the protector may be slid underneath the dura in a lateral direction along the dura. As the protector is slid underneath the dura, the dura will come in contact with the cutting edge 135 of the blade 130, thus creating a continuous incision.

According to some embodiments, the cutting function of the blade does not depend on movement of the blade relative to the handle or protector. Rather, the cutting function results from the dura being forced to slide onto the cutting edge of the blade. This principle of operation is what allows the user of the dural knife to make a continuous incision through the dura.

According to some embodiments, the cutting edge 135 of the blade 130 is not straight. According to some embodiments, the cutting edge 135 of the blade 130 is of a concave shape. According to some embodiments, the concave shape of the blade edge merges seamlessly with one or more of the handle and protector. According to some embodiments, the cutting edge 135 of the blade 130 is of a convex shape.

According to some embodiments, the shape of the protector is adapted to slide along the underside of the dura without abrading or rupturing it. According to some embodiments, the protector comprises a rounded tip 140, a flat top 125, and a flat bottom 126. According to some embodiments, the protector sides 127 are of a curved shape, giving the protector a bulbous appearance when viewed from above (See FIG. 3). According to some embodiments, all sides of the protector are smooth and transition into one another via smooth curvature. According to some embodiments, the smoothness of the surface of the protector can rub against the underside of the dura without significant resistance and without rupturing any innervating blood vessels or otherwise damaging the dura.

According to some embodiments, the height of the protector 120 is greater towards the heel 128 than toward the rounded tip 140. The height 171 of the protector is the longest vertical (y-axis) distance between the protector top 125 and protector bottom 126 along, and perpendicular to, the total length. According to some embodiments, the height of the protector increases continuously from the rounded tip 140 to the heel 128. According to some embodiments, the height of the protector increases continuously from the rounded tip 140 for approximately 10% of the total length 165, then remains constant for the remaining distance of the total length. According to some embodiments, the height of the protector increases continuously from the rounded tip 140 for approximately 15% of the total length 165, then remains constant for the remaining distance of the total length. According to some embodiments, the height of the protector increases continuously from the rounded tip 140 for approximately 20% of the total length 165, then remains constant for the remaining distance of the total length. According to some embodiments, the height of the protector increases continuously from the rounded tip 140 for approximately 25% of the total length 165, then remains constant for the remaining distance of the total length. According to some embodiments, the height of the protector increases continuously from the rounded tip 140 for approximately 30% of the total length 165, then remains constant for the remaining distance of the total length. According to some embodiments, the height of the protector increases continuously from the rounded tip 140 for approximately 35% of the total length 165, then remains constant for the remaining distance of the total length. According to some embodiments, the height of the protector increases continuously from the rounded tip 140 for approximately 40% of the total length 165, then remains constant for the remaining distance of the total length. According to some embodiments, the height of the protector increases continuously from the rounded tip 140 for approximately 45% of the total length 165, then remains constant for the remaining distance of the total length. According to some embodiments, the height of the protector increases continuously from the rounded tip 140 for approximately 50% of the total length 165, then remains constant for the remaining distance of the total length. According to some embodiments, the height of the protector increases continuously from the rounded tip 140 for approximately 55% of the total length 165, then remains constant for the remaining distance of the total length. According to some embodiments, the height of the protector increases continuously from the rounded tip 140 for approximately 60% of the total length 165, then remains constant for the remaining distance of the total length. According to some embodiments, the height of the protector increases continuously from the rounded tip 140 for approximately 65% of the total length 165, then remains constant for the remaining distance of the total length. According to some embodiments, the height of the protector increases continuously from the rounded tip 140 for approximately 70% of the total length 165, then remains constant for the remaining distance of the total length. According to some embodiments, the height of the protector increases continuously from the rounded tip 140 for approximately 75% of the total length 165, then remains constant for the remaining distance of the total length. According to some embodiments, the height of the protector increases continuously from the rounded tip 140 for approximately 80% of the total length 165, then remains constant for the remaining distance of the total length. According to some embodiments, the height of the protector increases continuously from the rounded tip 140 for approximately 85% of the total length 165, then remains constant for the remaining distance of the total length. According to some embodiments, the height of the protector increases continuously from the rounded tip 140 in the range of approximately 10% to 90% of the total length 165, then remains constant for the remaining distance of the total length.

According to some embodiments, the height of the protector increase continuously from the rounded tip 140 in the range of approximately 10% to 90% of the total length 165, then decreases for the remaining distance of the total length. According to some embodiments, the height of the protector increase continuously from the rounded tip 140 for approximately 10% of the total length 165, then decreases for the remaining distance of the total length. According to some embodiments, the height of the protector increase continuously from the rounded tip 140 for approximately 15% of the total length 165, then decreases for the remaining distance of the total length. According to some embodiments, the height of the protector increase continuously from the rounded tip 140 for approximately 20% of the total length 165, then decreases for the remaining distance of the total length. According to some embodiments, the height of the protector increase continuously from the rounded tip 140 for approximately 25% of the total length 165, then decreases for the remaining distance of the total length. According to some embodiments, the height of the protector increase continuously from the rounded tip 140 for approximately 30% of the total length 165, then decreases for the remaining distance of the total length. According to some embodiments, the height of the protector increase continuously from the rounded tip 140 for approximately 35% of the total length 165, then decreases for the remaining distance of the total length. According to some embodiments, the height of the protector increase continuously from the rounded tip 140 for approximately 40% of the total length 165, then decreases for the remaining distance of the total length. According to some embodiments, the height of the protector increase continuously from the rounded tip 140 for approximately 45% of the total length 165, then decreases for the remaining distance of the total length. According to some embodiments, the height of the protector increase continuously from the rounded tip 140 for approximately 50% of the total length 165, then decreases for the remaining distance of the total length. According to some embodiments, the height of the protector increase continuously from the rounded tip 140 for approximately 60% of the total length 165, then decreases for the remaining distance of the total length. According to some embodiments, the height of the protector increase continuously from the rounded tip 140 for approximately 65% of the total length 165, then decreases for the remaining distance of the total length. According to some embodiments, the height of the protector increase continuously from the rounded tip 140 for approximately 70% of the total length 165, then decreases for the remaining distance of the total length. According to some embodiments, the height of the protector increase continuously from the rounded tip 140 for approximately 75% of the total length 165, then decreases for the remaining distance of the total length. According to some embodiments, the height of the protector increase continuously from the rounded tip 140 for approximately 80% of the total length 165, then decreases for the remaining distance of the total length. According to some embodiments, the height of the protector increase continuously from the rounded tip 140 for approximately 85% of the total length 165, then decreases for the remaining distance of the total length. According to some embodiments, the height of the protector increase continuously from the rounded tip 140 for approximately 90% of the total length 165, then decreases for the remaining distance of the total length.

According to some embodiments, the height of the protector increases continuously from the rounded tip 140 in the range of approximately 10% to 90% of the total length 165, then remains constant for the remaining distance of the total length, wherein the protector bottom 126 remains flat over greater than 90% of the total length 165. According to some embodiments, the height of the protector increases continuously from the rounded tip 140 for approximately 10% of the total length 165, then remains constant for the remaining distance of the total length, wherein the protector bottom 126 remains flat over greater than 90% of the total length 165. According to some embodiments, the height of the protector increases continuously from the rounded tip 140 for approximately 15% of the total length 165, then remains constant for the remaining distance of the total length, wherein the protector bottom 126 remains flat over greater than 90% of the total length 165. According to some embodiments, the height of the protector increases continuously from the rounded tip 140 for approximately 20% of the total length 165, then remains constant for the remaining distance of the total length, wherein the protector bottom 126 remains flat over greater than 90% of the total length 165. According to some embodiments, the height of the protector increases continuously from the rounded tip 140 for approximately 25% of the total length 165, then remains constant for the remaining distance of the total length, wherein the protector bottom 126 remains flat over greater than 90% of the total length 165. According to some embodiments, the height of the protector increases continuously from the rounded tip 140 for approximately 30% of the total length 165, then remains constant for the remaining distance of the total length, wherein the protector bottom 126 remains flat over greater than 90% of the total length 165. According to some embodiments, the height of the protector increases continuously from the rounded tip 140 for approximately 35% of the total length 165, then remains constant for the remaining distance of the total length, wherein the protector bottom 126 remains flat over greater than 90% of the total length 165. According to some embodiments, the height of the protector increases continuously from the rounded tip 140 for approximately 40% of the total length 165, then remains constant for the remaining distance of the total length, wherein the protector bottom 126 remains flat over greater than 90% of the total length 165. According to some embodiments, the height of the protector increases continuously from the rounded tip 140 for approximately 45% of the total length 165, then remains constant for the remaining distance of the total length, wherein the protector bottom 126 remains flat over greater than 90% of the total length 165. According to some embodiments, the height of the protector increases continuously from the rounded tip 140 for approximately 50% of the total length 165, then remains constant for the remaining distance of the total length, wherein the protector bottom 126 remains flat over greater than 90% of the total length 165. According to some embodiments, the height of the protector increases continuously from the rounded tip 140 for approximately 55% of the total length 165, then remains constant for the remaining distance of the total length, wherein the protector bottom 126 remains flat over greater than 90% of the total length 165. According to some embodiments, the height of the protector increases continuously from the rounded tip 140 for approximately 60% of the total length 165, then remains constant for the remaining distance of the total length, wherein the protector bottom 126 remains flat over greater than 90% of the total length 165. According to some embodiments, the height of the protector increases continuously from the rounded tip 140 for approximately 65% of the total length 165, then remains constant for the remaining distance of the total length, wherein the protector bottom 126 remains flat over greater than 90% of the total length 165. According to some embodiments, the height of the protector increases continuously from the rounded tip 140 for approximately 70% of the total length 165, then remains constant for the remaining distance of the total length, wherein the protector bottom 126 remains flat over greater than 90% of the total length 165. According to some embodiments, the height of the protector increases continuously from the rounded tip 140 for approximately 75% of the total length 165, then remains constant for the remaining distance of the total length, wherein the protector bottom 126 remains flat over greater than 90% of the total length 165. According to some embodiments, the height of the protector increases continuously from the rounded tip 140 for approximately 80% of the total length 165, then remains constant for the remaining distance of the total length, wherein the protector bottom 126 remains flat over greater than 90% of the total length 165. According to some embodiments, the height of the protector increases continuously from the rounded tip 140 for approximately 85% of the total length 165, then remains constant for the remaining distance of the total length, wherein the protector bottom 126 remains flat over greater than 90% of the total length 165. According to some embodiments, the height of the protector increases continuously from the rounded tip 140 for approximately 90% of the total length 165, then remains constant for the remaining distance of the total length, wherein the protector bottom 126 remains flat over greater than 90% of the total length 165.

According to some embodiments, the height of the protector increases continuously from the rounded tip 140 in the range of approximately 10% to 90% of the total length 165, then decreases for the remaining distance of the total length, wherein the protector bottom 126 remains flat over greater than 90% of the total length 165. According to some embodiments, the height of the protector increases continuously from the rounded tip 140 for approximately 10% of the total length 165, then decreases for the remaining distance of the total length, wherein the protector bottom 126 remains flat over greater than 90% of the total length 165. According to some embodiments, the height of the protector increases continuously from the rounded tip 140 for approximately 15% of the total length 165, then decreases for the remaining distance of the total length, wherein the protector bottom 126 remains flat over greater than 90% of the total length 165. According to some embodiments, the height of the protector increases continuously from the rounded tip 140 for approximately 20% of the total length 165, then decreases for the remaining distance of the total length, wherein the protector bottom 126 remains flat over greater than 90% of the total length 165. According to some embodiments, the height of the protector increases continuously from the rounded tip 140 for approximately 25% of the total length 165, then decreases for the remaining distance of the total length, wherein the protector bottom 126 remains flat over greater than 90% of the total length 165. According to some embodiments, the height of the protector increases continuously from the rounded tip 140 for approximately 30% of the total length 165, then decreases for the remaining distance of the total length, wherein the protector bottom 126 remains flat over greater than 90% of the total length 165. According to some embodiments, the height of the protector increases continuously from the rounded tip 140 for approximately 35% of the total length 165, then decreases for the remaining distance of the total length, wherein the protector bottom 126 remains flat over greater than 90% of the total length 165. According to some embodiments, the height of the protector increases continuously from the rounded tip 140 for approximately 40% of the total length 165, then decreases for the remaining distance of the total length, wherein the protector bottom 126 remains flat over greater than 90% of the total length 165. According to some embodiments, the height of the protector increases continuously from the rounded tip 140 for approximately 45% of the total length 165, then decreases for the remaining distance of the total length, wherein the protector bottom 126 remains flat over greater than 90% of the total length 165. According to some embodiments, the height of the protector increases continuously from the rounded tip 140 for approximately 50% of the total length 165, then decreases for the remaining distance of the total length, wherein the protector bottom 126 remains flat over greater than 90% of the total length 165. According to some embodiments, the height of the protector increases continuously from the rounded tip 140 for approximately 55% of the total length 165, then decreases for the remaining distance of the total length, wherein the protector bottom 126 remains flat over greater than 90% of the total length 165. According to some embodiments, the height of the protector increases continuously from the rounded tip 140 for approximately 60% of the total length 165, then decreases for the remaining distance of the total length, wherein the protector bottom 126 remains flat over greater than 90% of the total length 165. According to some embodiments, the height of the protector increases continuously from the rounded tip 140 for approximately 65% of the total length 165, then decreases for the remaining distance of the total length, wherein the protector bottom 126 remains flat over greater than 90% of the total length 165. According to some embodiments, the height of the protector increases continuously from the rounded tip 140 for approximately 70% of the total length 165, then decreases for the remaining distance of the total length, wherein the protector bottom 126 remains flat over greater than 90% of the total length 165. According to some embodiments, the height of the protector increases continuously from the rounded tip 140 for approximately 75% of the total length 165, then decreases for the remaining distance of the total length, wherein the protector bottom 126 remains flat over greater than 90% of the total length 165. According to some embodiments, the height of the protector increases continuously from the rounded tip 140 for approximately 80% of the total length 165, then decreases for the remaining distance of the total length, wherein the protector bottom 126 remains flat over greater than 90% of the total length 165. According to some embodiments, the height of the protector increases continuously from the rounded tip 140 for approximately 85% of the total length 165, then decreases for the remaining distance of the total length, wherein the protector bottom 126 remains flat over greater than 90% of the total length 165. According to some embodiments, the height of the protector increases continuously from the rounded tip 140 for approximately 90% of the total length 165, then decreases for the remaining distance of the total length, wherein the protector bottom 126 remains flat over greater than 90% of the total length 165.

According to some embodiments, the height of the protector increases continuously from the rounded tip 140 in the range of approximately 10% to 90% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 10% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 15% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 20% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 25% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 30% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 35% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 40% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 45% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 50% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 55% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 60% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 65% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 70% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 75% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 80% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 85% of the total length 165, then decreases or remains constant for the remaining distance of the total length, wherein the protector bottom 126 remains flat over greater than 90% of the total length 165. According to some embodiments, the height of the protector increases continuously from the rounded tip 140 for approximately 90% of the total length 165, then decreases or remains constant for the remaining distance of the total length, wherein the protector bottom 126 remains flat over greater than 90% of the total length 165.

According to some embodiments, the width of the protector 120 is greater toward the heel 128 than toward the rounded tip 140. The width of the protector is the horizontal distance between the protector sides 127 along, and perpendicular to, the total length 165. According to some embodiments, the width of the protector increases continuously from the rounded tip 140 to the heel 128. According to some embodiments, the width of the protector increases continuously from the rounded tip 140 in the range of approximately 10% to 90% of the total length 165, then remains constant for the remaining distance of the total length 165. According to some embodiments, the width of the protector increases continuously from the rounded tip 140 for approximately 10% of the total length 165, then remains constant for the remaining distance of the total length 165. According to some embodiments, the width of the protector increases continuously from the rounded tip 140 for approximately 15% of the total length 165, then remains constant for the remaining distance of the total length 165. According to some embodiments, the width of the protector increases continuously from the rounded tip 140 for approximately 20% of the total length 165, then remains constant for the remaining distance of the total length 165. According to some embodiments, the width of the protector increases continuously from the rounded tip 140 for approximately 25% of the total length 165, then remains constant for the remaining distance of the total length 165. According to some embodiments, the width of the protector increases continuously from the rounded tip 140 for approximately 30% of the total length 165, then remains constant for the remaining distance of the total length 165. According to some embodiments, the width of the protector increases continuously from the rounded tip 140 for approximately 35% of the total length 165, then remains constant for the remaining distance of the total length 165. According to some embodiments, the width of the protector increases continuously from the rounded tip 140 for approximately 40% of the total length 165, then remains constant for the remaining distance of the total length 165. According to some embodiments, the width of the protector increases continuously from the rounded tip 140 for approximately 45% of the total length 165, then remains constant for the remaining distance of the total length 165. According to some embodiments, the width of the protector increases continuously from the rounded tip 140 for approximately 50% of the total length 165, then remains constant for the remaining distance of the total length 165. According to some embodiments, the width of the protector increases continuously from the rounded tip 140 for approximately 55% of the total length 165, then remains constant for the remaining distance of the total length 165. According to some embodiments, the width of the protector increases continuously from the rounded tip 140 for approximately 60% of the total length 165, then remains constant for the remaining distance of the total length 165. According to some embodiments, the width of the protector increases continuously from the rounded tip 140 for approximately 65% of the total length 165, then remains constant for the remaining distance of the total length 165. According to some embodiments, the width of the protector increases continuously from the rounded tip 140 for approximately 70% of the total length 165, then remains constant for the remaining distance of the total length 165. According to some embodiments, the width of the protector increases continuously from the rounded tip 140 for approximately 75% of the total length 165, then remains constant for the remaining distance of the total length 165. According to some embodiments, the width of the protector increases continuously from the rounded tip 140 for approximately 80% of the total length 165, then remains constant for the remaining distance of the total length 165. According to some embodiments, the width of the protector increases continuously from the rounded tip 140 for approximately 85% of the total length 165, then remains constant for the remaining distance of the total length 165. According to some embodiments, the width of the protector increases continuously from the rounded tip 140 for approximately 90% of the total length 165, then remains constant for the remaining distance of the total length 165.

According to some embodiments, the width of the protector increases continuously from the rounded tip 140 in the range of approximately 10% to 90% of the total length 165, then decreases for the remaining distance of the total length 165. According to some embodiments, the width of the protector increases continuously from the rounded tip 140 for approximately 10% of the total length 165, then decreases for the remaining distance of the total length 165. According to some embodiments, the width of the protector increases continuously from the rounded tip 140 for approximately 15% of the total length 165, then decreases for the remaining distance of the total length 165. According to some embodiments, the width of the protector increases continuously from the rounded tip 140 for approximately 20% of the total length 165, then decreases for the remaining distance of the total length 165. According to some embodiments, the width of the protector increases continuously from the rounded tip 140 for approximately 25% of the total length 165, then decreases for the remaining distance of the total length 165. According to some embodiments, the width of the protector increases continuously from the rounded tip 140 for approximately 30% of the total length 165, then decreases for the remaining distance of the total length 165. According to some embodiments, the width of the protector increases continuously from the rounded tip 140 for approximately 35% of the total length 165, then decreases for the remaining distance of the total length 165. According to some embodiments, the width of the protector increases continuously from the rounded tip 140 for approximately 40% of the total length 165, then decreases for the remaining distance of the total length 165. According to some embodiments, the width of the protector increases continuously from the rounded tip 140 for approximately 45% of the total length 165, then decreases for the remaining distance of the total length 165. According to some embodiments, the width of the protector increases continuously from the rounded tip 140 for approximately 50% of the total length 165, then decreases for the remaining distance of the total length 165. According to some embodiments, the width of the protector increases continuously from the rounded tip 140 for approximately 55% of the total length 165, then decreases for the remaining distance of the total length 165. According to some embodiments, the width of the protector increases continuously from the rounded tip 140 for approximately 60% of the total length 165, then decreases for the remaining distance of the total length 165. According to some embodiments, the width of the protector increases continuously from the rounded tip 140 for approximately 65% of the total length 165, then decreases for the remaining distance of the total length 165. According to some embodiments, the width of the protector increases continuously from the rounded tip 140 for approximately 70% of the total length 165, then decreases for the remaining distance of the total length 165. According to some embodiments, the width of the protector increases continuously from the rounded tip 140 for approximately 75% of the total length 165, then decreases for the remaining distance of the total length 165. According to some embodiments, the width of the protector increases continuously from the rounded tip 140 for approximately 80% of the total length 165, then decreases for the remaining distance of the total length 165. According to some embodiments, the width of the protector increases continuously from the rounded tip 140 for approximately 85% of the total length 165, then decreases for the remaining distance of the total length 165. According to some embodiments, the width of the protector increases continuously from the rounded tip 140 for approximately 90% of the total length 165, then decreases for the remaining distance of the total length 165.

According to some embodiments, the width of the protector increases continuously from the rounded tip 140 in the range of approximately 10% to 90% of the total length 165, then remains constant or decreases for the remaining distance of the total length 165. According to some embodiments, the width of the protector increases continuously from the rounded tip 140 for approximately 10% of the total length 165, then remains constant or decreases for the remaining distance of the total length 165. According to some embodiments, the width of the protector increases continuously from the rounded tip 140 for approximately 15% of the total length 165, then remains constant or decreases for the remaining distance of the total length 165. According to some embodiments, the width of the protector increases continuously from the rounded tip 140 for approximately 20% of the total length 165, then remains constant or decreases for the remaining distance of the total length 165. According to some embodiments, the width of the protector increases continuously from the rounded tip 140 for approximately 25% of the total length 165, then remains constant or decreases for the remaining distance of the total length 165. According to some embodiments, the width of the protector increases continuously from the rounded tip 140 for approximately 30% of the total length 165, then remains constant or decreases for the remaining distance of the total length 165. According to some embodiments, the width of the protector increases continuously from the rounded tip 140 for approximately 35% of the total length 165, then remains constant or decreases for the remaining distance of the total length 165. According to some embodiments, the width of the protector increases continuously from the rounded tip 140 for approximately 40% of the total length 165, then remains constant or decreases for the remaining distance of the total length 165. According to some embodiments, the width of the protector increases continuously from the rounded tip 140 for approximately 45% of the total length 165, then remains constant or decreases for the remaining distance of the total length 165. According to some embodiments, the width of the protector increases continuously from the rounded tip 140 for approximately 50% of the total length 165, then remains constant or decreases for the remaining distance of the total length 165. According to some embodiments, the width of the protector increases continuously from the rounded tip 140 for approximately 55% of the total length 165, then remains constant or decreases for the remaining distance of the total length 165. According to some embodiments, the width of the protector increases continuously from the rounded tip 140 for approximately 60% of the total length 165, then remains constant or decreases for the remaining distance of the total length 165. According to some embodiments, the width of the protector increases continuously from the rounded tip 140 for approximately 65% of the total length 165, then remains constant or decreases for the remaining distance of the total length 165. According to some embodiments, the width of the protector increases continuously from the rounded tip 140 for approximately 70% of the total length 165, then remains constant or decreases for the remaining distance of the total length 165. According to some embodiments, the width of the protector increases continuously from the rounded tip 140 for approximately 75% of the total length 165, then remains constant or decreases for the remaining distance of the total length 165. According to some embodiments, the width of the protector increases continuously from the rounded tip 140 for approximately 80% of the total length 165, then remains constant or decreases for the remaining distance of the total length 165. According to some embodiments, the width of the protector increases continuously from the rounded tip 140 for approximately 85% of the total length 165, then remains constant or decreases for the remaining distance of the total length 165. According to some embodiments, the width of the protector increases continuously from the rounded tip 140 for approximately 90% of the total length 165, then remains constant or decreases for the remaining distance of the total length 165.

Figure 4:
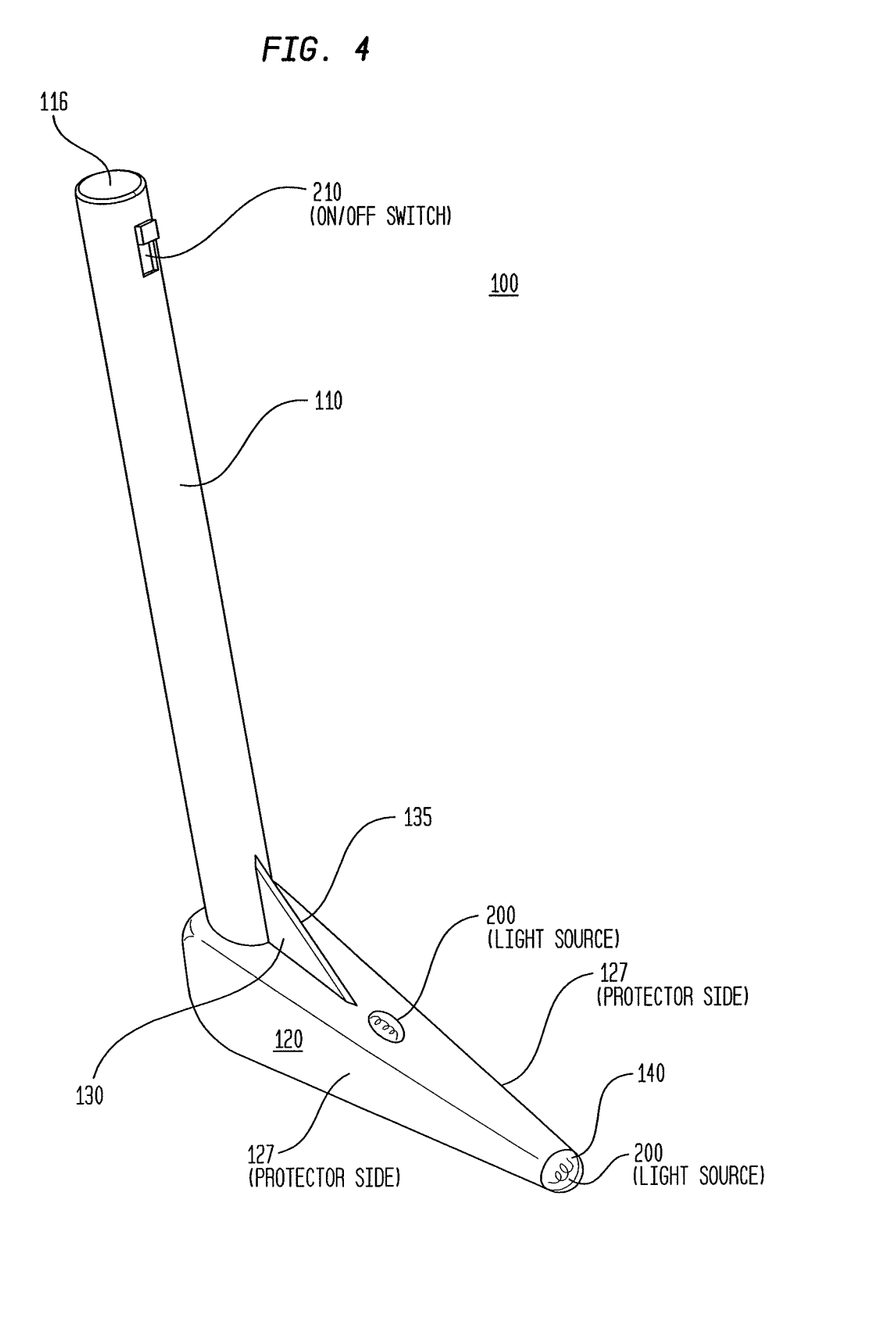
FIG. 4 illustrates a perspective view of one embodiment of the described invention comprising a light source in the protector.

According to some embodiments, the protector further comprises a light source embedded on one or more surfaces of the protector. According to some embodiments, the protector further comprises two or more light sources in one or more surfaces of the protector. According to some embodiments, this light source projects light through the dura. Such transillumination allows the user of the dural knife to see blood vessels that vascularize the dura before they are cut by the blade. In this manner, the user of the dural knife can avoid inadvertent injury to an underlying bridging vein. According to some embodiments, the light source is attached to or embedded in the rounded tip 140. According to some embodiments, the light source is attached to or embedded in the protector top 125. According to some embodiments, the light source is attached to or embedded in the protector bottom 126. According to some embodiments, the power source for the light is contained within the handle or protector, such as a battery. According to some embodiments, the power source for the light is external to the dural knife, and under that circumstance a power connector is present within the handle or protector. According to some embodiments, there is a mechanism on the dural knife that turns on and off the light source. According to some embodiments, a button or a trigger is located on the handle 110 which can reversibly turn on or off the light source. According to some embodiments, the mechanism that controls the light source is not binary, i.e. does not simply turn the light on or off. Rather, according to some embodiments, there is a dimmer mechanism on the dural knife that allows the user to increase or decrease the intensity of light while on according to user preference. Thus, according to some embodiments, the user of the dural knife can manually control illumination by the light source from zero percent intensity (off) to 100 percent intensity. According to some embodiments, the user of the dural knife can set the light source to 0% intensity. According to some embodiments, the user of the dural knife can set the light source to 5% intensity. According to some embodiments, the user of the dural knife can set the light source to 10% intensity. According to some embodiments, the user of the dural knife can set the light source to 15% intensity. According to some embodiments, the user of the dural knife can set the light source to 20% intensity. According to some embodiments, the user of the dural knife can set the light source to 25% intensity. According to some embodiments, the user of the dural knife can set the light source to 30% intensity. According to some embodiments, the user of the dural knife can set the light source to 35% intensity. According to some embodiments, the user of the dural knife can set the light source to 40% intensity. According to some embodiments, the user of the dural knife can set the light source to 45% intensity. According to some embodiments, the user of the dural knife can set the light source to 50% intensity. According to some embodiments, the user of the dural knife can set the light source to 55% intensity. According to some embodiments, the user of the dural knife can set the light source to 60% intensity. According to some embodiments, the user of the dural knife can set the light source to 65% intensity. According to some embodiments, the user of the dural knife can set the light source to 70% intensity. According to some embodiments, the user of the dural knife can set the light source to 75% intensity. According to some embodiments, the user of the dural knife can set the light source to 80% intensity. According to some embodiments, the user of the dural knife can set the light source to 85% intensity. According to some embodiments, the user of the dural knife can set the light source to 90% intensity.

According to some embodiments, the protector 120 further comprises a suction conduit for removing fluid. According to some embodiments, the suction conduit is of a tube shape. According to some embodiments, the opening of the suction conduit is attached to or embedded in the rounded tip 140. According to some embodiments, the opening of the suction conduit is attached to or embedded in the protector top 125. According to some embodiments, the opening of the suction conduit is attached to or embedded in the protector bottom 126. According to some embodiments, the opening of the suction conduit leads to a suction apparatus connector located in a position distal to the opening, such as in the heel 128 of the protector or the handle top 116. The suction apparatus connector can be connected to the suction apparatus that creates negative pressure. According to some embodiments, there is a mechanism on the dural knife that turns on and off the suction at the opening of the suction conduit. According to some embodiments, a mechanism is located on the handle 110 which reversibly turns on and off the suction at the opening of the suction conduit. According to some embodiments, the mechanism that controls the suction at the opening of the suction conduit is not binary; i.e. does not simply have an off or on state; rather, the mechanism on the dural knife allows the user to increase or decrease the intensity of suction according to user preference. According to some embodiments, the mechanism comprises a second opening to the suction conduit, wherein the second opening is larger than the first opening of the suction conduit, the second opening being of a size and shape that can be covered by a human finger. Thus, according to some embodiments, the user of the dural knife can manually control suction at the opening of the suction conduit from zero percent suction intensity (off) to 100 percent suction intensity. According to some embodiments, the user of the dural knife can manually set suction at the opening of the suction conduit to 0% intensity. According to some embodiments, the user of the dural knife can manually set suction at the opening of the suction conduit to 5% intensity. According to some embodiments, the user of the dural knife can manually set suction at the opening of the suction conduit to 10% intensity. According to some embodiments, the user of the dural knife can manually set suction at the opening of the suction conduit to 15% intensity. According to some embodiments, the user of the dural knife can manually set suction at the opening of the suction conduit to 20% intensity. According to some embodiments, the user of the dural knife can manually set suction at the opening of the suction conduit to 25% intensity. According to some embodiments, the user of the dural knife can manually set suction at the opening of the suction conduit to 30% intensity. According to some embodiments, the user of the dural knife can manually set suction at the opening of the suction conduit to 35% intensity. According to some embodiments, the user of the dural knife can manually set suction at the opening of the suction conduit to 40% intensity. According to some embodiments, the user of the dural knife can manually set suction at the opening of the suction conduit to 45% intensity. According to some embodiments, the user of the dural knife can manually set suction at the opening of the suction conduit to 50% intensity. According to some embodiments, the user of the dural knife can manually set suction at the opening of the suction conduit to 55% intensity. According to some embodiments, the user of the dural knife can manually set suction at the opening of the suction conduit to 60% intensity. According to some embodiments, the user of the dural knife can manually set suction at the opening of the suction conduit to 65% intensity. According to some embodiments, the user of the dural knife can manually set suction at the opening of the suction conduit to 70% intensity. According to some embodiments, the user of the dural knife can manually set suction at the opening of the suction conduit to 75% intensity. According to some embodiments, the user of the dural knife can manually set suction at the opening of the suction conduit to 80% intensity. According to some embodiments, the user of the dural knife can manually set suction at the opening of the suction conduit to 85% intensity. According to some embodiments, the user of the dural knife can manually set suction at the opening of the suction conduit to 90% intensity.

According to some embodiments, the dural knife comprises a cautery component capable of cauterizing human tissue. According to some embodiments, the cautery component acts as the cutting component and is in place of the blade 130. According to some embodiments, the cautery component is powered by a battery located within the dural knife. According to some embodiments, the cautery component is powered by a power source external to the dural knife. According to some embodiments, the cautery component comprises a wire loop. According to some embodiments, the cautery component comprises a microtip. According to some embodiments, the dural knife comprises a cautery component, a handle and protector made of non-conductive material.

The various components of the described invention may be made from one or more materials in various embodiments of the inventions. For example, according to some embodiments, the components can be made from one or more of steel, aluminum, plastic, ceramics, wood, rubber, graphite, hybrid mixtures of metal and composites, or any other suitable material.

The described invention provides several advantages. First, according to some embodiment of the present invention, the height of the cutting edge is low relative to the combined height of the cutting edge and the protector. This feature prevents a surgeon from dipping the device too low and dragging the protector across the nervous tissue of the brain. In other words, even if a doctor uses the highest part of the cutting edge of the present invention to cut the dura during surgery, it will minimize the tendency for the surgeon to gouge the nervous tissue because the highest part of the blade is relatively close to the bottom of the protector. Second, according to some embodiments, the invention comprises a substantial area on the top of the protector that does not have a cutting edge. This feature allows the surgeon to put pressure on the underside of the dura, thus raising the dura, prior to any cutting, which ensures that the dura can be effectively raised from the underlying nervous tissue. Third, according to some embodiments, the protector has a curved shape that raises the dura from the underlying nervous tissue while sliding the protector under the dura. This feature ensures that the dura becomes raised while cutting of the dura continuously progresses.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

The invention claimed is:

1. A dural knife comprising:
   a handle comprising a front, a back, a first end, and a second end;
   a protector comprising a top, a bottom, a rounded tip, a first side, a second side, and a heel, the second end of the handle connected to the top of the protector at the heel end;
   a cutting clement blade connected to the handle and the protector, the cutting clement blade having a cutting edge that merges with the front of the handle and with the top of the protector; wherein a vertical distance between a point where the cutting edge of the cutting element blade merges with the front of the handle and the most distal part of the bottom of the protector that defines the combined height of the cutting element blade and the protector wherein
   (a) a horizontal distance between the rounded tip and the heel defines a total length of the protector, and wherein the vertical distance between a most distal part of the top and a most distal part of the bottom defines the height of the protector;
   (b) the bottom remains flat over the total length of the protector;
   (c) said first side and said second side of the protector smoothly transition between said top said bottom without any sharp edges;
   (d) the exterior of the protector is limited to materials that allow the protector to effectively slide along an underside of the dura without abrading or rupturing the dura or blood vessels and nerves that course between the brain and the dura; and
   (e) wherein a region on the top of the protector between the rounded tip and the a point where the cutting edge of the blade merges with the top of the protector defines a fore top, and a horizontal distance between the point where the cutting edge of the blade merges with the top of the protector and the rounded tip defines the length of the fore top; wherein the tore top of the protector has a length of at least 25% of the total length of the protector; and
   (f) wherein a vertical distance between the point at which the cutting edge of the blade merges with the front of the handle and the point at which the cutting edge of the blade merges with the protector defines the height of the cutting element of the blade; wherein the height of the cutting element blade is at most 80% of the vertical distance between the point where the cutting edge merges with or intersects the front of the handle and the lowest point on the bottom of the protector height of the cutting element the protector; and
   (g) the height of the protector increases continuously from the rounded tip for over 10% to 90% of the total length of the protector, then decreases or remains constant for a remaining distance of the total length, and
   (h) the width of the protector increases continuously from the rounded tip for over 10% to 90% of the total length of the protector, then decreases or remains constant for a remaining distance; and
   (i) wherein the dural knife is adapted to safely raise the dura away from nervous tissue of the brain or spinal cord, associated surface blood vessels, and to identify blood vessels and nerves that course between the brain and the dura during continuous incision of the dura; and
   (j) wherein the handle is positioned to form at least a 91° angle as defined by the first the first end, the second end, and the rounded tip, and (k) wherein the handle is positioned to form not more than a 135° angle as defined by the first the first end, the second end, and the rounded tip.

2. The dural knife of claim 1, wherein the cutting element height of the blade is approximately 50% of the combined height of the cutting element and vertical distance between the point where the cutting edge merges with or intersects the front of the handle and the lowest point on the bottom of the protector.

3. The dural knife of claim 1, wherein the length of the fore top is at least 30% of the total length of the protector.

4. The dural knife of claim 1, wherein the protector further comprises a first light source in the rounded tip, wherein the first light source is adapted to project light through the fascial plane, such as the dura under which said light source is inserted so as to see blood vessels that vascularize the dura and identify blood vessels and nerves that course between the brain and the dura; and a second light source disposed upon the top proximal to where the cutting edge of the cutting element blade merges with the top of the protector.

5. The dural knife of claim 4, wherein the handle further comprises a mechanism that controls the light source.

6. The dural knife of claim 1, wherein the protector further comprises a suction opening and channel, through which fluids can be drawn away from the protector.

7. The dural knife of claim 6, wherein the handle further comprises a mechanism that controls a force of suction drawing fluids away from the protector.

8. The dural knife of claim 1, wherein the cutting edge of the cutting element blade is straight and is positioned at an angle of approximately 90 degrees or more relative to the fore top of the protector, where the cutting edge of the cutting element blade merges with the top of the protector.

9. The dural knife of claim 1, wherein the cutting clement is blade is replaced by a cauterizer.

10. The dural knife of claim 9, wherein the protector further comprises a light source in the rounded tip, wherein the light source is adapted to project light through the dura so as to see blood vessels that vascularize the dura and to identify blood vessels and nerves that course between the brain and the dura.

11. The dural knife of claim 9, wherein the protector further comprises a suction opening and channel, through which fluids can be drawn away from the protector.

12. The dural knife of claim 11, wherein the handle further comprises a mechanism that controls a force of suction drawing fluids away from the protector.

13. A dural knife comprising:
a handle comprising a front, a back, a first end, and a second end;
a protector comprising a top, a bottom, a rounded tip, and a heel,
the second end of the handle connected to the top of the protector at the heel end; wherein
(a) a horizontal distance between the rounded tip and the heel defines a total length of the protector, and wherein the vertical distance between a most distal part of the top and a most distal part of the bottom defines the height of the protector;
(b) the height of the protector increases continuously from the rounded tip to the heel of the protector;
(c) the protector further comprises a light source in the rounded tip, wherein the light source is adapted to project light through the dura so as to see blood vessels that vascularize the dura and to identify blood vessels and nerves that course between the brain and the dura;
(d) the protector bottom remains flat over 90% or more of the total length of the protector;
(e) shape of the protector is adapted to slide along an underside of the dura without abrading or rupturing the dura or blood vessels and nerves that course between the brain and the dura;
a blade connected to the handle and the protector, the blade comprising a cutting edge that merges with the front of the handle and with the top of the protector; wherein
(i) a vertical distance between a point where the cutting edge of the blade merges with the front of the handle and the most distal part of the bottom of the protector defines the combined height of the blade and protector;
(ii) a vertical distance between the point at which the cutting edge of the blade merges with the front of the handle and the point at which the cutting edge of the blade merges with the protector defines the height of the of the blade; and
(iii) the height of the blade is at most 85% of the vertical distance between the point where the cutting edge merges with or intersects the front of the handle and the lowest point on the bottom of the protector;
a region on the top of the protector between the rounded tip and the a point where the cutting edge of the blade merges with the top of the protector defines a fore top, and a horizontal distance between the point where the cutting edge of the blade merges with the top of the protector and the rounded tip defines the length of the fore top; wherein the fore top of the protector has a length of at least 25% of the total length of the protector;
wherein the dural knife is adapted to safely raise the dura away from nervous tissue of the brain or spinal cord and associated surface blood vessels and to identify blood vessels and nerves that course between the brain and the dura during continuous incision of the dura.

14. A dural knife comprising:
a handle comprising a front, a back, a first end, and a second end;
a protector comprising a top, a bottom, a rounded tip, and a heel, the second end of the handle connected to the top of the protector at the heel end; wherein
(a) a horizontal distance between the rounded tip and the heel defines a total length of the protector, and wherein the vertical distance between a most distal part of the top and a most distal part of the bottom defines the height of the protector;
(b) the height of the protector increases continuously from the rounded tip to the heel of the protector;
(c) the protector bottom remains flat over 90% or more of the total length of the protector;
(d) shape of the protector is adapted to slide along an underside of the dura without abrading or rupturing the dura or blood vessels and nerves that course between the brain and the dura; and
(e) the protector further comprises a suction opening and channel, through which fluids can be drawn away from the protector;
a blade connected to the handle and the protector, the blade comprising a cutting edge that merges with the front of the handle and with the top of the protector; wherein
(i) a vertical distance between a point where the cutting edge of the blade merges with the front of the handle and the most distal part of the bottom of the protector defines the combined height of the blade and protector;
(ii) a vertical distance between the point at which the cutting edge of the blade merges with the front of the handle and the point at which the cutting edge of the blade merges with the protector defines the height of the of the blade; and (iii) the height of the blade is at most 85% of the vertical distance between the point where the cutting edge merges with or intersects the front of the handle and the lowest point on the bottom of the protector;

a region on the top of the protector between the rounded tip and the a point where the cutting edge of the blade merges with the top of the protector defines a fore top, and a horizontal distance between the point where the cutting edge of the blade merges with the top of the protector and the rounded tip defines the length of the fore top; wherein the fore top of the protector has a length of at least 25% of the total length of the protector;

wherein the dural knife is adapted to safely raise the dura away from nervous tissue of the brain or spinal cord and associated surface blood vessels and to identify blood vessels and nerves that course between the brain and the dura during continuous incision of the dura.

15. The dural knife according to claim 14, wherein the handle further comprises a mechanism that controls a force of suction drawing fluids away from the protector.

16. A dural knife comprising: a handle comprising a front, a back, a first end, and a second end;

a protector comprising a top, a bottom; a rounded tip, and a heel, the second end of the handle connected to the top of the protector at the heel end; wherein (a) a horizontal distance between the rounded tip and the heel defines a total length of the protector, and wherein the vertical distance between a most distal part of the top and a most distal part of the bottom defines the height of the protector;

(b) the height of the protector increases continuously from the rounded tip to the heel of the protector;

(c) the protector bottom remains flat over 90% or more of the total length of the protector;

(d) shape of the protector is adapted to slide along an underside of the dura without abrading or rupturing the dura or blood vessels and nerves that course between the brain and the dura;

(e) the protector further comprises
  (1) a suction opening and channel, through which fluids can be drawn away from the protector; and
  (2) a light source in the rounded tip, wherein the light source is adapted to project light through the dura so as to see blood vessels that vascularize the dura and to identify to identify blood vessels and nerves that course between the brain and the dura;

a blade connected to the handle and the protector, the blade comprising a cutting edge that merges with the front of the handle and with the top of the protector; wherein (i) a vertical distance between a point where the cutting edge of the blade merges with the front of the handle and the most distal part of the bottom of the protector defines the combined height of the blade and protector;

(ii) a vertical distance between the point at which the cutting edge of the blade merges with the front of the handle and the point at which the cutting edge of the blade merges with the protector defines the height of the of the blade; and (iii) the height of the blade is at most 85% of the vertical distance between the point where the cutting edge merges with or intersects the front of the handle and the lowest point on the bottom of the protector;

(iv) a region on the top of the protector between the rounded tip and the a point where the cutting edge of the blade merges with the top of the protector defines a fore top, and a horizontal distance between the point where the cutting edge of the blade merges with the top of the protector and the rounded tip defines the length of the fore top; wherein the fore top of the protector has a length of at least 25% of the total length of the protector;

(v) wherein the dural knife is adapted to safely raise the dura away from nervous tissue of the brain or spinal cord and associated surface blood vessels to identify blood vessels and nerves that course between the brain and the dura during continuous incision of the dura.

17. The dural knife according to claim 16, wherein the handle further comprises a mechanism that controls a force of suction drawing fluids away from the protector.

* * * * *